(12) United States Patent
Von Drasek et al.

(10) Patent No.: US 6,943,886 B2
(45) Date of Patent: Sep. 13, 2005

(54) METHOD FOR ENHANCED GAS MONITORING IN HIGH PARTICLE DENSITY FLOW STREAMS

(75) Inventors: William A. Von Drasek, Oak Forest, IL (US); Kenneth A. Mulderink, Countryside, IL (US); Ovidiu Marin, Lisle, IL (US)

(73) Assignees: Air Liquide America, L.P., Houston, TX (US); L'Air Liquide- Societe Anonyme a'Directoire et Conseil de Surveillance pour l'Etude et l'Exploitation des Procedes Georges Claude, Paris (FR)

(*) Notice: Subject to any disclaimer, the term of this patent is extended or adjusted under 35 U.S.C. 154(b) by 330 days.

(21) Appl. No.: 10/353,786

(22) Filed: Jan. 29, 2003

(65) Prior Publication Data

US 2003/0218752 A1 Nov. 27, 2003

Related U.S. Application Data

(60) Provisional application No. 60/356,103, filed on Feb. 11, 2002.

(51) Int. Cl.[7] .............................................. G01N 21/00
(52) U.S. Cl. ...................... 356/439; 356/437; 356/440
(58) Field of Search ................................. 356/437, 439, 356/337–340

(56) References Cited

U.S. PATENT DOCUMENTS

| 2,624,012 A | * | 12/1952 | English, Jr. et al. ......... 356/439 |
| 3,251,999 A | * | 5/1966 | Middleton et al. ........... 356/439 |
| 3,462,608 A | * | 8/1969 | Weston et al. ............... 356/439 |
| 4,515,896 A | * | 5/1985 | Melton ........................ 356/417 |
| 4,534,651 A | * | 8/1985 | Minikane ..................... 356/440 |
| 5,512,757 A | * | 4/1996 | Cederstrand et al. ........ 356/437 |

* cited by examiner

*Primary Examiner*—Zandra V. Smith
(74) *Attorney, Agent, or Firm*—Linda K. Russell; Christopher J. Cronin (57) ABSTRACT

A method for conducting laser absorption measurements in high temperature process streams having high levels of particulate matter is disclosed. An impinger is positioned substantially parallel to a laser beam propagation path and at upstream position relative to the laser beam. Beam shielding pipes shield the beam from the surrounding environment. Measurement is conducted only in the gap between the two shielding pipes where the beam propagates through the process gas. The impinger facilitates reduced particle presence in the measurement beam, resulting in improved SNR (signal-to-noise) and improved sensitivity and dynamic range of the measurement.

16 Claims, 8 Drawing Sheets

METHOD FOR ENHANCED GAS MONITORING IN HIGH PARTICLE DENSITY FLOW STREAMS

CROSS REFERENCE TO RELATED APPLICATION

This application claims the benefit of U.S. Provisional Application No. 60/356,103, filed Feb. 11, 2002.

BACKGROUND OF THE INVENTION

1. Field of the Invention

A method for conducting laser absorption measurements in high temperature process streams having high levels of particulate matter is disclosed. An impinger is positioned substantially parallel to a laser beam propagation path and at upstream position relative to the laser beam. Beam shielding pipes shield the beam from the surrounding environment. Measurement is conducted only in the gap between the two shielding pipes where the beam propagates through the process gas. The impinger facilitates reduced particle presence in the measurement beam, resulting in improved SNR (signal-to-noise) and improved sensitivity and dynamic range of the measurement.

2. Description of Prior Art

Monitoring the off-gas composition from combustion processes is useful for determining the extent of combustion taking place, conducting mass and energy audits, and monitoring the level of pollutants generated. Monitoring the gas composition is particularly useful for process control to perform corrective and/or optimization adjustments on selected process parameters. Identifying which process parameters to adjust is dependent on the parameter and the process. For example, processes showing an excess of CO in the exhaust are exhibiting incomplete combustion and a potential loss of energy. Optimizing the process would require an increase in the oxidant input or a decrease in the fuel input. Alternatively, other parameters can be adjusted, such as the process pressure that will affect the level of air infiltration into the process.

Many industrial processes, such as electric arc furnaces (EAF), waste incineration, and gasification, pose a special problem for off-gas composition due to the high gas temperature and the level of particles present. Conventional extractive gas sampling techniques using a water-cooled probe, to withdraw a sample from the process, followed by conditioning, using a chiller and filter to remove moisture and particles, suffer from probe plugging and corrosion. Probe plugging and corrosion problems can place a high maintenance demand on an analysis system, making it unattractive for routine use. In addition, extractive gas monitoring suffers slow response times that can be several tens of seconds to minutes to record the gas analysis result. Slow response time becomes a significant factor on dynamic processes such as an EAF, where conditions can be changing at a rate faster the diagnostic response, resulting in delays for applying process control. The combination of probe maintenance and slow response time issues make the technique unattractive on extremely harsh combustion systems.

In situ measurements using optical techniques, such as diode lasers, have been demonstrated on harsh combustion processes. In this case, a diode laser is tuned at the frequency of an absorption transition of the molecule of interest. A number of examples in the literature demonstrate the use of diode lasers to monitor the exhaust gas from a process.

For secondary steel processing, EAF's are used in a batch mode to melt the steel. These processes are particularly harsh, with exhaust gas temperatures less than about 1600 C and particle densities of 10 $g/Nm^3$ to 100 $g/Nm^3$. Stantec and Air Liquide have demonstrated extractive sampling monitoring of the off-gas, but probe maintenance often limits the usefulness and duration of conducting continuous day-to-day monitoring of the processes.

Sandia National Laboratory demonstrated analysis of the off-gas using diode lasers operating in the mid-IR working with the American Iron and Steel Institute. Their patent publication WO 99/26058 discloses the use of a diode laser propagating through the gap between the furnace exhaust and the main exhaust to measure CO, $CO_2$ and $H_2O$. However, working in the mid-IR range requires cryogenic cooling of the laser, and the system is not compatible with fiber optic components. The laser beam propagates across the whole length of the exhaust, resulting in an average measurement of the gas concentration along the beam path. In addition, the exhaust region of the EAF is affected by air being entrained into the flow along the gap. This air entrainment is used to cool the exhaust gas and burn off any residual CO from the process itself. Therefore, conducting a path-averaged measurement at the gap position will lead to error, due to the uncertainty in the true path length of the measurement. Additionally, the combination of the long path-length through the duct (typically four to eight feet long) and particle densities results in severe laser beam attenuation. The combination of these two effects can be detrimental to the measurement and place limitations on the accuracy of measured concentration values.

Similarly, a conceptual layout using near-IR lasers for CO and $H_2O$ monitoring instead of mid-IR with beam propagating across the duct, without any shielding, has been shown. For both mid-IR and near-IR measurements, shielding the beam from the ambient atmosphere is not required, since CO is present only in the EAF gap area and the $H_2O$ lines are only present at high temperatures.

Inclusion of $O_2$ monitoring in the near-IR on an EAF as demonstrated by Dietrich et al. does require shielding the beam from the ambient air. Dietrich, et al., LASER ANALYSIS OF CO AND OXYGEN IN EAF OFF-GAS, $59^{th}$ Electric Furnace Conference and $19^{th}$ Process Technology Conference Proceedings, Iron and Steel Society (2001). In this case, shielding pipes are used on each side of the furnace gap to launch and receive the beam for monitoring $O_2$ and CO. Placement of the shielding pipes in the EAF exhaust sets the pathlength to the desired distance to reduce the effect of particles and remove uncertainties regarding the pathlength. Despite the shortened path length, difficulties in obtaining adequate light transmission persisted due to the high particulate levels present. Similarly Thomson, et al., shows a conceptual application using a near-IR laser system. Thomson, et al., LASER BASED OPTICAL MEASUREMENTS OF ELECTRIC ARC FURNACE OFF-GAS FOR POLLUTION CONTROL AND ENERGY EFFICIENCY, Innovative Technologies for Steel and Other Materials, Met. Soc., The Conference of Metallurgists, Toronto (August 2000).

Thus, a problem associated with methods for gas monitoring in high particle density flow streams is that they provide a slow response time and thereby do not adequately indicate process conditions to enable optimal process control.

Still another problem associated with methods for gas monitoring in high particle density flow streams that precede the present invention is that they do not facilitate optimal use of the potential energy present in the process by-products for heat generation.

Yet another problem associated with methods for gas monitoring in high particle density flow streams that precede the present invention is that they are susceptible to probe plugging and corrosion.

An even further problem associated with methods for gas monitoring in high particle density flow streams that precede the present invention is that they require undue replacement of the monitoring equipment.

Still a further problem associated with methods for gas monitoring in high particle density flow streams that precede the present invention is that they do not provide continuous, near real-time measurements of the species concentration in the waste gases, with acceptable accuracy, so as to facilitate an adapted dynamic monitoring of process characteristics.

Another problem associated with methods for gas monitoring in high particle density flow streams that precede the present invention is that they do not adequately facilitate control of the CO and $H_2$ combustion by-products.

Yet another problem associated with methods for gas monitoring in high particle density flow streams is that they are not readily adaptable for use in industrial processes that experiences high particle densities, temperature gradients, mechanical vibration, rapid variations in temperature and gas composition, and high radiation loads from the process itself.

Another problem associated with methods for gas monitoring in high particle density flow streams is that they do not adequately provide continuous monitoring of the process conditions.

Still another problem associated with methods for gas monitoring in high particle density flow streams is that they cannot be adapted readily for use in high temperature environments and still provide a durable method that does not require unduly frequent replacement of equipment.

In contrast to the foregoing, the present invention provides a enhanced gas monitoring in high particle density flow streams that seeks to overcome the foregoing problems and provide a more simplistic, more easily constructed and relatively reliable methodology.

For the foregoing reasons, there has been defined a long felt and unsolved need for a method for enhanced gas monitoring in high particle density flow streams that seeks to overcome the problems discussed above, while at the same time providing a simple, easily constructed and maintained design that facilitates more reliable process control.

SUMMARY OF THE INVENTION

In the invention described a method for enhancing the light transmission through a particle-laden medium is described. Enhancement of the light transmission will improve the overall signal quality thus improving the measurements accuracy and reliability. In another aspect of the invention a method for reducing mechanical vibration and optical access issues are presented.

Thus, an object of the present invention is to provide a method for enhanced gas monitoring in high particle density flow streams that has a more immediate response time and thereby indicates process conditions more quickly, to enable optimal process control.

Still another object of the present invention is to provide a method for enhanced gas monitoring in high particle density flow streams that facilitates optimal use of the potential energy present in the process by-products, for heat generation.

Yet another object of the present invention is to provide a method for enhanced gas monitoring in high particle density flow streams that is not susceptible to probe plugging and corrosion.

An even further object of the present invention is to provide a method for enhanced gas monitoring in high particle density flow streams that does not require undue replacement of the monitoring equipment.

Yet another object of the present invention is to provide a method for enhanced gas monitoring in high particle density flow streams that provides continuous, near real-time measurements of the species concentration in the waste gases, with acceptable accuracy, so as to facilitate an adapted dynamic monitoring of process characteristics.

An even further object of the present invention is to provide a method for enhanced gas monitoring in high particle density flow streams that facilitates better control of the CO and $H_2$ combustion by-products.

Still another object of the present invention is to provide a method for enhanced gas monitoring in high particle density flow streams that can be used in industrial processes that experiences high particle densities, temperature gradients, mechanical vibration, rapid variations in temperature and gas composition, and high radiation loads from the process itself.

Yet another object of the present invention is to provide a method for enhanced gas monitoring in high particle density flow streams that utilizes a more simply constructed, inexpensive and reliable sampling apparatus.

Another object of the present invention is to provide a method for enhanced gas monitoring in high particle density flow streams that provides continuous monitoring of the process conditions.

Yet another object of the present invention is to provide a method for enhanced gas monitoring in high particle density flow streams that can be adapted for use in high temperature environments, and yet which provides a durable method that does not require unduly frequent replacement of equipment.

These and other objects, advantages and features of the present invention will be apparent from the detailed description that follows.

BRIEF DESCRIPTION OF THE DRAWINGS

In the detailed description that follows, reference will be made to the following figures:

FIG. A is illustrates fluid flow characteristics for particles injected at locations upstream of a bluff body;

FIG. 6' illustrates a schematic representation of an alternative subassembly installed on an EAF exhaust;

DETAILED DESCRIPTION OF A PREFERRED EMBODIMENT

A method for conducting laser absorption measurements in high temperature process streams having high levels of particulate matter is disclosed. An impinger is positioned substantially parallel to a laser beam propagation path and at upstream position relative to the laser beam. Beam shielding pipes shield the beam from the surrounding environment. Measurement is conducted only in the gap between the two shielding pipes where the beam propagates through the process gas. The impinger facilitates reduced particle presence in the measurement beam, resulting in improved SNR (signal-to-noise) and improved sensitivity and dynamic range of the measurement. In a preferred embodiment, the method is adapted for use in an electric arc furnace (EAF).

To address reduce the effects of pathlength, particulate matter, and mechanical vibration from an industrial process exhaust stream, such as an EAF, a set of water-cooled pipes can be used to act as a shielding around the laser beam. A minimum of one pipe is needed, with the preferred arrangement consisting of two shielding pipes: one for the beam launch and the other as the beam receiver. This provides a means to set the path length within the duct to the desired distance. Further improvement in the measurement is obtained by adding a particle impinger positioned upstream of the gas flow and substantially parallel to the beam propagation path. The impinger can be water, steam or gas cooled, and can be constructed and arranged to couple the launch and receiver pipes.

The impinger provides two improvements for harsh monitoring environments. First, coupling the whole assembly reduces mechanical vibration, since the assembly is now a single unit. Further rigidity and resistance to mechanical vibration is obtained by coupling the beam launch and receiver into a system where they are substantially parallel to one another, allowing additional bracing to be used. Second, the impinger will cause stratification between the gas and particles, as the two-phase fluid flows around the impinger. Reduction of the particle concentration in the measurement path increases the measurement SNR, resulting in improved sensitivity and dynamic range. Details of these aspects will be discussed below.

Using water-cooled pipes that act as a beam shield mounted on the process along the line-of-sight path of the laser beam, the gap between the two guides sets the effective pathlength of the absorption measurement. The laser source can be positioned in a remote location from the process, with the beam directed through guides to the detector, which can also be positioned in a remote location from the process. In this configuration the sensitive equipment, viz., the detector and the fiber optic to deliver the near infrared beam, is located away from the process. This configuration permits improved monitoring of the process, by further isolating the detection apparatus from the mechanical vibrations and other detrimental physical characteristics of the process.

In use, the roof of an EAF is moved to allow charging of the tank with scrap metal, inducing vibration. Second, the process itself experiences significant vibration due to perturbation of the process itself. These process vibrations can be overcome by maintaining the ratio of the aperture (diameter of the beam shield) to the beam diameter to be greater than about 2.

During steel melting, the hot exhaust gas plus the high particle densities result in an optically thick exhaust stream that is strongly radiating. The high level of background black body radiation from the particles requires that the laser radiation be discriminated from the background. Background rejection using filters or dispersive optics such as gratings can be used. However, filters can introduce reflections that result in constructive interference on the detected signal. Allowing the laser beam to propagate through the receiver shield to a detector placed far from the process reduces the background radiation intensity due to the inverse square law, which states that the intensity of the radiation per unit area varies in inverse proportion to he square of the distance.

Preferred locations of the beam shields are on the stationary exhaust and not the furnace roof exhaust. This allows continuous monitoring throughout the melt cycle where the batch furnace may be tilted several degrees to allow the slag layer above the melt to move. Mounting the shield on the furnace roof would result in loss of monitoring during the tilting stage.

Thus, means to continuously monitor the gas composition from an extremely harsh environment, characteristically at high temperature and with high particle density, is provided. Using a beam shield on the process for applications using absorption techniques to monitor the gas molecule of interest provides a well-defined pathlength that can be positioned anywhere within the process area of interest. On high particle density processes where the laser power is attenuated by the presence of particles, shortening and defining the beam path enhances the detection capability, sensitivity and accuracy. Further enhancement of the signal are obtained by adding an impinger that is substantially parallel to the beam and positioned upstream of the beam.

Figure 1:
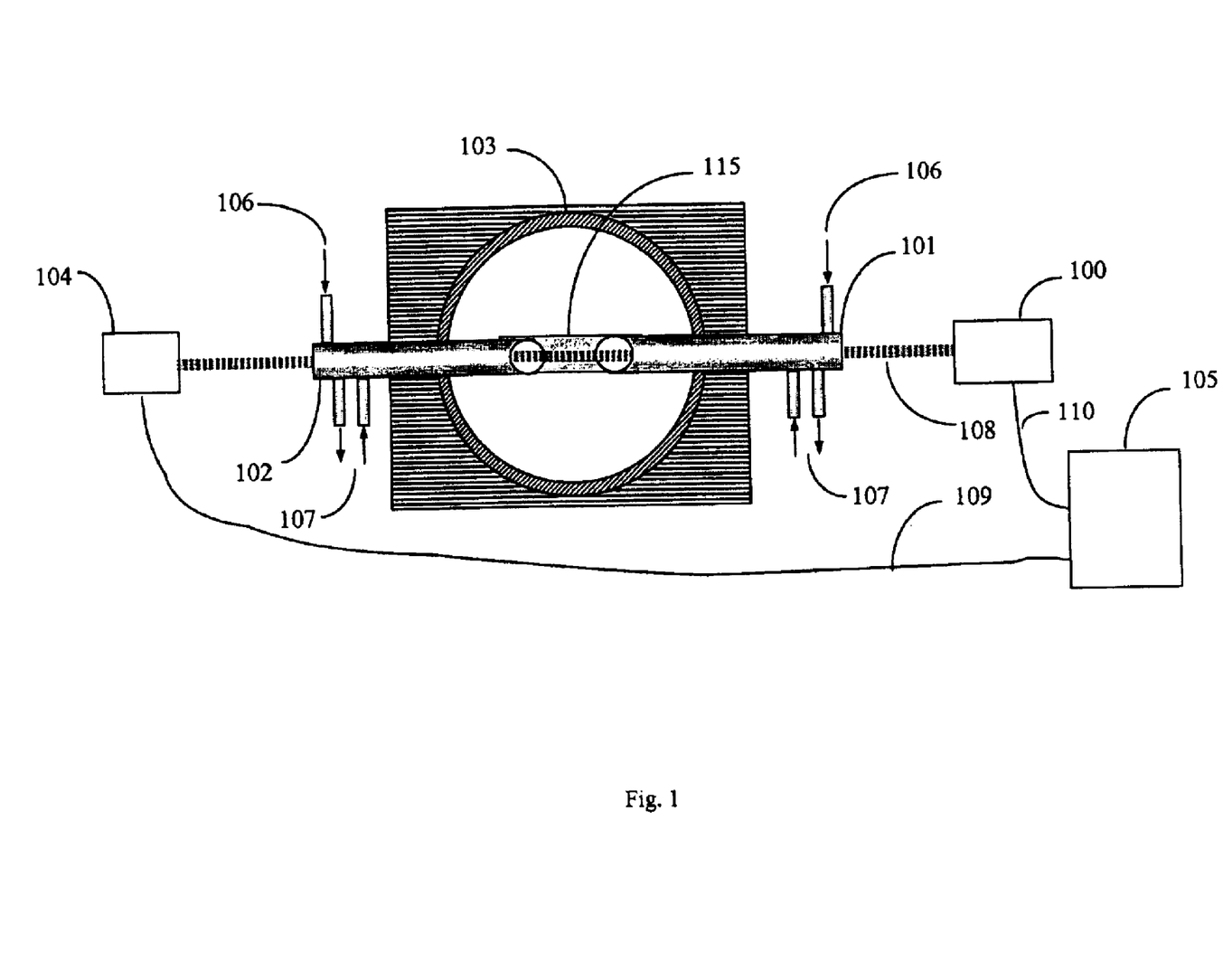
FIG. 1 illustrates a schematic of a first preferred embodiment of a gas monitor.

FIG. 1 illustrates a schematic of a first preferred embodiment of a gas monitor. Laser beam 108 is launched from module 104 with the beam directed into the cooled pipe 102. At the opposite side, a matching cooled pipe 101 receives the beam that is then monitored by the detector housed in module 100. The launch module and receiver module shown in FIG. 1 are detached from the shielding pipes. Alternatively, one or both of these modules can be directly attached to the pipes. The detected signal is transported to unit 105, which processes the measurement and houses the laser or lasers and their associated electronics. Fiber optic cable 109 transports the beam to the launching module 104. The shielding pipes can be water, steam, or gas cooled, and provided with the cooling fluid inlet/outlet 107. Internal purge gas 106 maintains a positive pressure in the pipes.

As shown in FIG. 1, the system is mounted on the exhaust of an EAF 103 that is water cooled. An impinger 115 couples the two shielding pipes. Without the impinger 115, the pathlength is defined by the distance between the launch and receiving pipes. With the impinger 115, the shielding pipes are coupled, making them less resistant to independent vibration modes, since the assembly will behave as a common unit.

Figure 2:
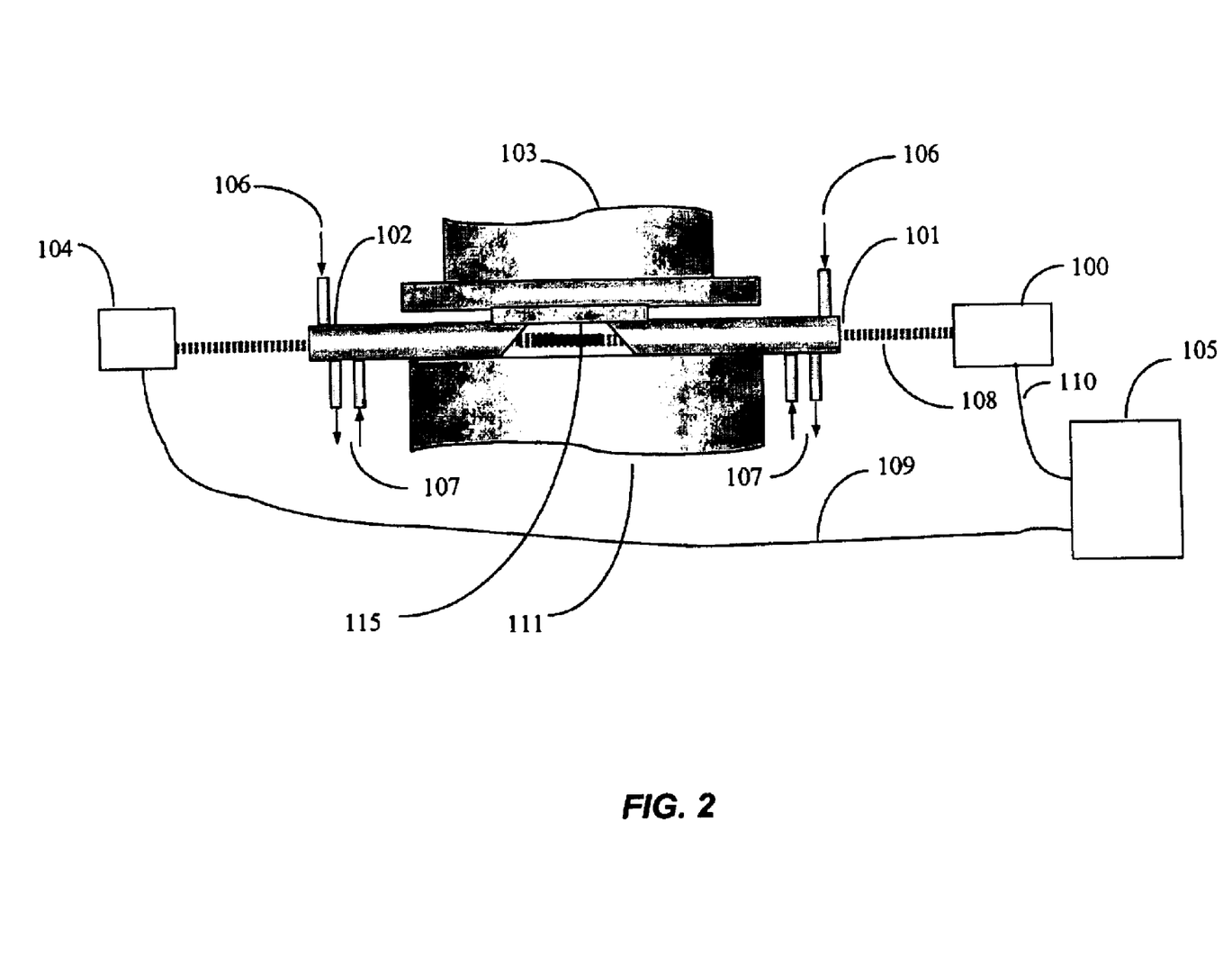
FIG. 2 illustrates a top plan schematic of a first preferred embodiment of a gas monitor.

FIG. 2 shows a similar view as FIG. 1 but from the top with the EAF exhaust system closed. The exhaust elbow 103 from the EAF roof aligns with the exhaust duct 111. The gap between ducts 103 and 111 permits air entrainment into the duct for cooling, and enhances CO burn-off. The gap width is selected depending on process operating conditions.

Figure 3:
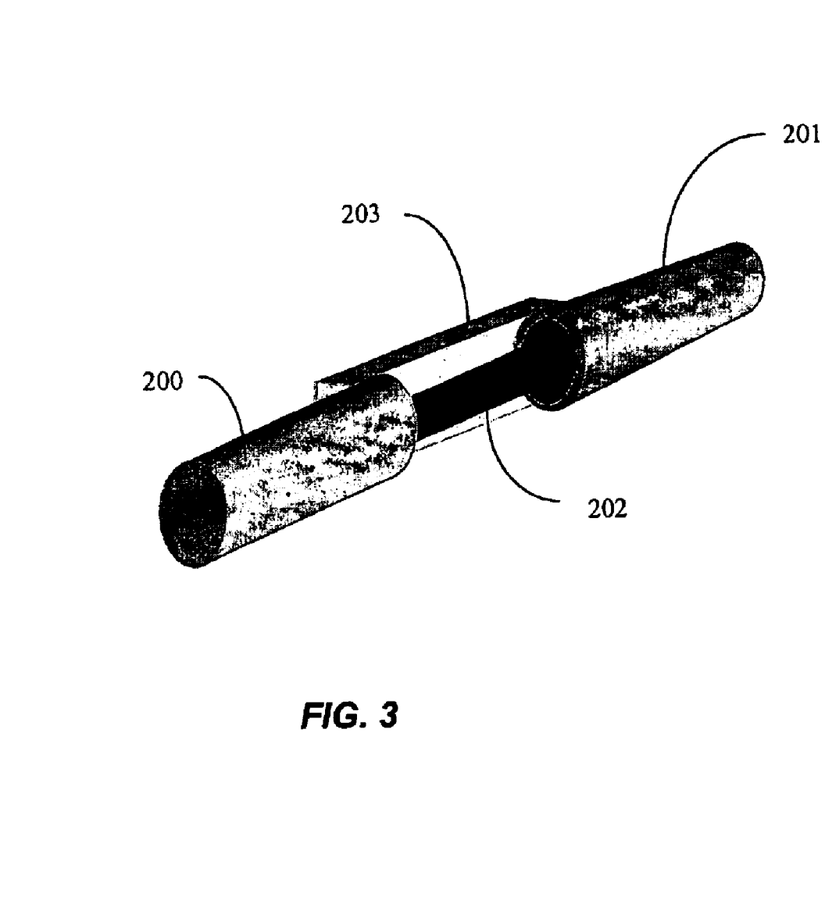
FIG. 3 illustrates a schematic representation of a shielding pipe adapted for use with an impinger.
Figure 4:
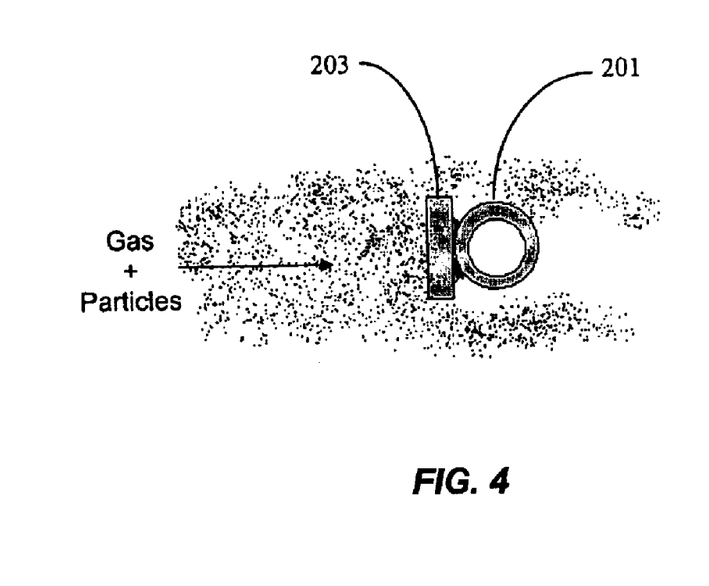
FIG. 4 illustrates a cut-away view of a shielding pipe adapted for use with an impinger.

FIGS. 3 and 4 illustrates the shielding pipes adapted with the impinger. As shown in FIG. 3, the laser beam 202 is launched through shielding pipe 201 and received in shielding pipe 200. Coupling the shield pipes 200 and 201 is the impinger block 203 positioned substantially parallel to the beam propagation path. Similar to the shielding pipes 200, 201, the impinger block 203 is cooled either with the same cooling media as the shielding pipe or its own independent source.

By coupling the two launch and receiver shielding pipes together the unit becomes more durable, decreasing the chance of misalignment. In addition, mechanical vibration transferred to the unit would be at the same frequency throughout the unit. In contrast, a decoupled construction in which the launch pipe and receiver pipe can vibrate at different frequencies, introduces a noise component to the signal. This additional noise results from the beam itself spatially moving about, hitting or missing the receiver detector.

The impinger block also reduces the particulate density in the measurement beam path. This effect is illustrated in FIG. 4, which shows a view of the launch shield pipe 201 and the impinger block 203 positioned such that the surface of the impinger is perpendicular to the gas plus particle flow. As shown in FIG. 4, the particles are blocked by the impinger surface, thus effectively stopping a substantial portion of the particles from traveling into the laser beam measurement volume. In highly turbulent flows, as experienced in the EAF exhaust, some particles would still flow into the laser beam volume, due to recirculation zones that result from a flow past an object.

The criteria describing the inertia effect of particles is the Stokes number (STK):

$$STK \cdot \frac{\rho_p d_p^2 \varepsilon}{18\mu k}$$

where $\rho_p$ is the particle density, $d_p$ is the particle diameter, $\mu$ is the fluid viscosity, k the turbulent kinetic energy, and $\varepsilon$ is the turbulent viscous dissipation. The expression represents the particle relaxation time:

$$\left(\frac{\rho_p d_p^2}{18\mu}\right)$$

to the turbulent time ($\varepsilon$/k). For the inertia effects to become important, STK>1, causing the particle trajectories to deviate from the gas flow field. The field of two-phase is an active research area because of the complexity of handling particle-gas systems and there is limited literature describing the flow past bluff bodies. An example of a recent study by Brandon shows instantaneous images (see FIG. A) of particles injected at 21 locations upstream of a bluff body for different STK numbers with a fixed Reynolds number of 1000 and a density ratio between particle and fluid of 1000. Brandon, et al., A NUMERICAL INVESTIGATION OF PARTICLE DEPOSITION ON A SQUARE CYLINDER PLACED IN A CHANNEL FLOW, Aerosol Science and Technology, v. 34, p. 340-352 (2001).

Clearly, dispersion between the gas and particles are observed for the range of STK number studied. A recirculation zone is produced by the gas on the downstream side of the bluff body that will track the gas composition change in time. Therefore, laser absorption measurements made at this location would be representative of the gas steam. Locating the measurement beam downstream of the bluff body would experience enhanced detection sensitivity due to the decreased particle density in this region as illustrated by Brandon's simulations. A similar finding was predicted by Laitone for Reynolds numbers up to 100,000, although these calculations were for a dilute gas-particle system. Laitone, A NUMERICAL SOLUTION FOR GAS-PARTICLE FLOWS AT HIGH REYNOLDS NUMBERS, Journal of Applied Mechanics, Winter Annual Meeting, Paper No. 81-WA/APM-10 (1981). It is noted that the shape of the bluff body 203 presented in FIG. 3 can be straight as shown, or can be round, parabolical, etc. Its shape will be optimized depending on the environment in which it will operate (velocities, composition, duct content, etc.).

Figure 5:
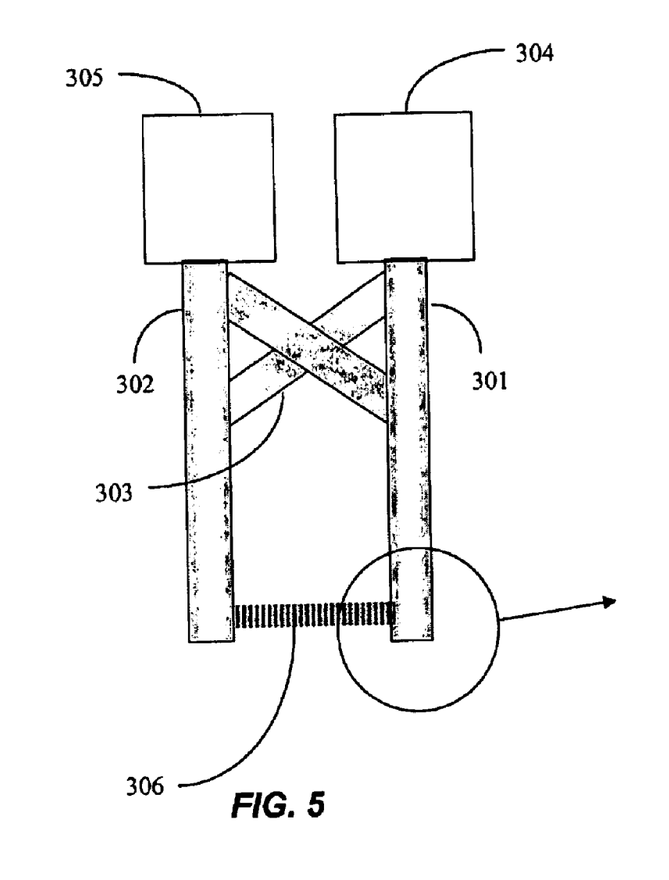
FIG. 5 illustrates a schematic representation of two laser beam launching and receiving assemblies adapted for use in an EAF.

For an EAF application, where vibration and instrument mounting location can be problematic, the preferred configuration for laser beam launching and receiving is shown in FIG. 5. In this case, the beam is launched from module 305 mounted on the shielding pipe, but a detached system as previously described can also be used. The launched beam is transported through shield pipe 302 and propagates across the path 306 into the receiving shield pipe 301, and finally to the detection module 304. For this configuration, a mirrored surface is used to direct the beam out or into the shield pipe at 90 degrees, as shown on the RHS of FIG. 5.

Purge gas maintains positive pressure in the shield pipe and cleans the mirrored surface. For high temperature applications, metallic mirrored surfaces are preferred. The purge gas also provides additional cooling to the mirror (in addition to that present by conduction from the shield pipe cooling fluid). To support the launch and receiver shield pipes, a bracing support 303 is provided. The bracing support 303 is constructed and arranged in a scissors-like pattern so as to maintain the components of the assembly in substantially parallel relation while at the same time providing selectability of the beam path length. The structural stability is greatly increased over the previous configurations, since both shield pipes are substantially parallel to one another, reducing the possibility of flexing or sagging that can occur in the aligned system shown in FIG. 1.

Figure 6:
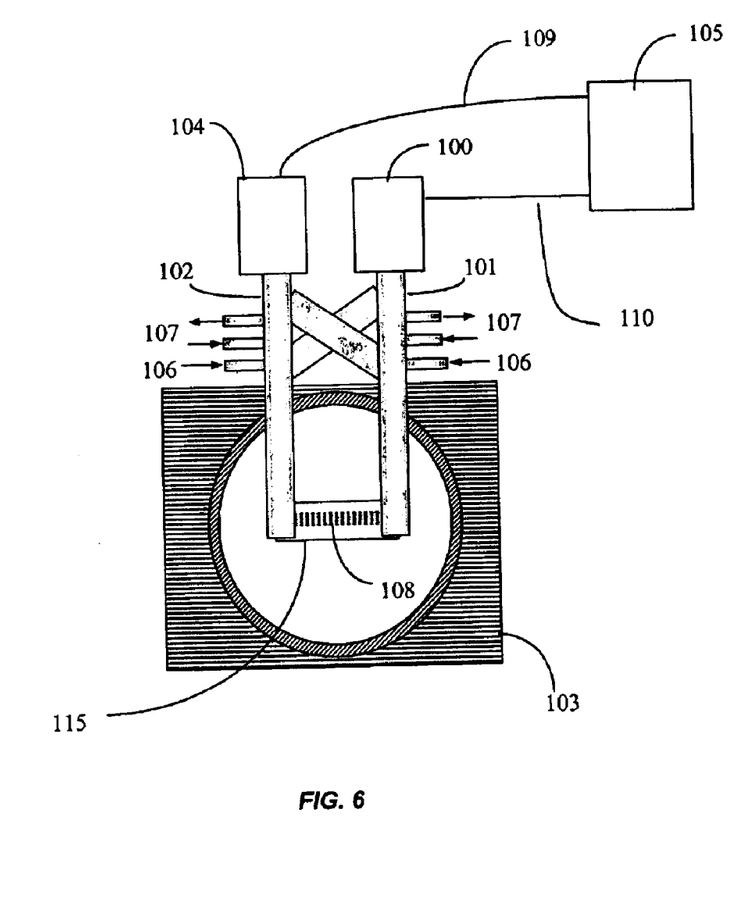
FIG. 6 illustrates a schematic representation of the subassembly shown in FIG. 5 installed on an EAF exhaust.
Figure 7:
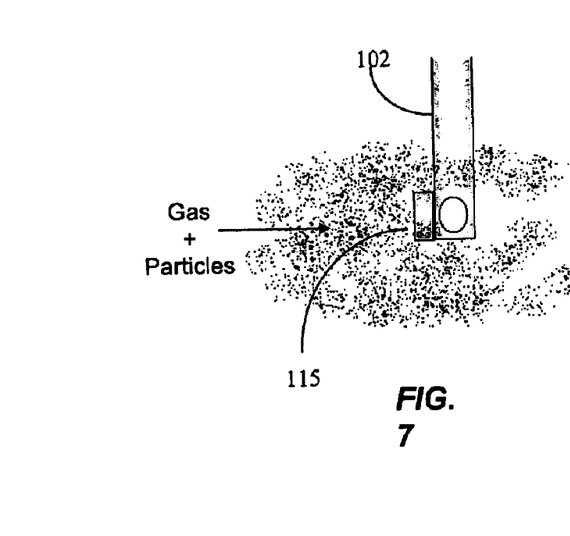
FIG. 7 illustrates a schematic illustration of an impinger block adapted for use with the subassembly shown in FIG. 6.

The system configured in FIG. 5 is relatively compact and therefore mobile. It can be mounted on the EAF exhaust duct or it can be inserted and removed through an automated manipulator. FIG. 6 illustrates an installation on the EAF exhaust and includes the impinger block. The effect of the impinger block is illustrated in FIG. 7.

FIG. 6' shows an alternative implementation in a system such as an EAF. The launch module 104 and the detector module 100 are installed on a frame 501, which can be installed from the above the duct or, alternately, from the ground. The frame 501 can be fixed or movable, in order to allow the motion of the other components of the EAF. In one option, when the frame is installed from the roof, the device is upwardly moveable in and out of the flue gas duct (direction I in FIG. 6'). Alternately, when installed from the ground, the frame is vertically and horizontally moveable (directions II in FIG. 6').

Note that the embodiment shown in FIG. 6' does not include the shield pipes 301 and 302 shown in FIG. 6. Although these can be eliminated from the embodiment, the well defined pathlength and $O_2$ detection is diminished, since the beam is exposed to ambient air. This embodiment is therefore only preferred where the pathlength is sufficiently short and particle concentration is sufficiently low that sufficient transmission of laser energy is detectable. At the same time, given the specific design, the structure can be stable, eliminating vibration, etc.

The embodiment shown in FIG. 6 can be installed on a combustion process where line-of-sight optical access is not feasible, requiring only a pair of access ports on the same side of the process. Other example process applications include large volume processes, such as float glass tanks or reheat furnaces. In these cases, line-of-sight monitoring can be over large distances in the process. Since absorption provides an average measure of the concentration or temperature in the volume of gas intersected by the laser beam, transient effects in specific zones can be averaged out. The periscope design allows shortening the path thereby, defining the measurement zone in a process. For example, measurements of $O_2$ and CO concentration conducted above the surface area of a steel billet may provide information on scale or decarburization. Typical billet lengths can range from about 20 to about 50 feet, and a measurement conducted by line-of-sight along the billet may not provide enough sensitivity due to the averaging effect. However, the periscope embodiment permits a selected or several selected zones near the billet to be monitored, thus enhancing the sensitivity of the measurement.

Figure 8:
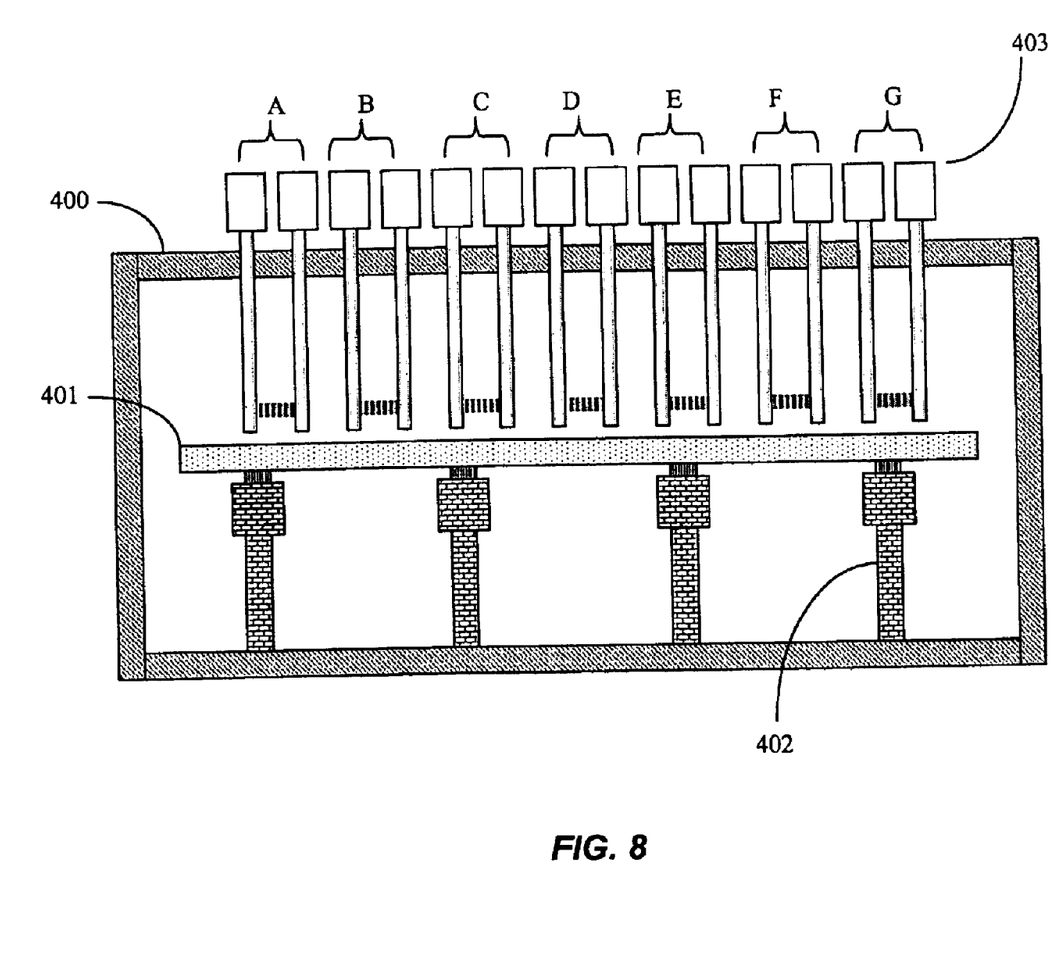
FIG. 8 illustrates a cross sectional view of a reheat furnace showing a billet supported by a walking beam mechanism.

Using several periscope systems, as shown in FIG. 8, concentration and temperature profiles across the process can be obtained. FIG. 8 shows a cross-sectional view of reheat furnace 400 with a billet 401 supported by the walking beam mechanism 402. In this illustration, several periscope systems 403 are implemented to provide seven measurement zones near the billet surface. Though there are a number of periscope system installed in the process, a single laser can be used in a multiplexed configuration to transport the light to each launching periscope. Depending on the application, i.e., level of particles in the process and number of measurement points, additional lasers or fiber amplified lasers systems may be needed to achieve the desired power levels to conduct the measurement. Impinger blocks are not shown in this application since particulate matter in reheat furnaces is small and has a negligible effect on the measured signal. If high levels of particulates are present, impinger blocks can be added.

Thus, a method for conducting laser absorption measurements in high temperature process streams having high levels of particulate matter is disclosed. The method utilizes an impinger that is positioned parallel to the laser beam propagation path and at upstream position relative to the laser beam. The laser beams are transported to and from the process by use of beam shielding pipes that shield the beam from the surrounding environment. The measurement is conducted only in the gap between the two shielding pipes where the beam propagates through the process gas. With the impinger present, the particle concentration in the measurement beam path is reduced, resulting in improved SNR (signal-to-noise) that impacts the sensitivity and dynamic range of the measurement. In addition, the impinger couples the launch and receiver system, thereby reducing mechanical vibration effects that can be encountered from a decoupled system.

Thus, a method for conducting laser absorption measurements in process streams containing particulates is disclosed. A laser beam is launched from a launch module along a laser beam propagation path extending from the launch module, through a first shielding pipe constructed and arranged to shield the beam from the surrounding environment, along a sampling propagation path through a sampling zone containing the sample to be monitored, through a second shielding pipe constructed and arranged to shield the beam from the surrounding environment, and to a receiver module. An impinger constructed and arranged to deflect the flow of at least a portion of the particulates in the process stream from the sampling zone is positioned substantially parallel to the sampling propagation path and upstream relative to the laser beam propagation path. The beam received by the receiver module is detected and compared to the beam launched from the launch module.

The impinger and the cooling pipes can either be maintained in fixed relation to one another or in detached relation to one another. Likewise, the launch module and the receiver module can be positioned in attached or detached relation from the shielding pipes, the impinger, or each other. The shielding pipes can have approximately equal diameters and can even be substantially identical in shape and size. The beam can be selected to have a diameter not less than about half of the diameter of the shielding pipes.

The shielding pipes and the impinger can be cooled. A positive pressure flow can be maintained within the shielding pipes, to keep particulates and the sample to be monitored from entering the ends of the shielding pipes, thereby maintaining an effective beam path length about equal to the distance between the shielding pipes. The distance between the shielding pipes is selectable so as to permit selection of the effective beam path length.

In an alternative arrangement, a method for conducting laser absorption measurements in process streams containing particulates is practiced as follows. A laser beam is launched from a launch module along a laser beam propagation path extending from the launch module, to a first beam redirection apparatus for redirecting the beam from the launch module approximately 90 degrees toward a sampling zone, through a sampling propagation path through a sampling zone containing the sample to be monitored, to a second beam redirection apparatus for redirecting the beam from the sampling zone approximately 90 degrees toward a receiver module, and to a receiver module. The beam is detected by the receiver module and compared to the beam launched from the launch module.

The first and second beam redirection apparatus each comprises a mirror constructed and arranged to reflect a beam of light about 90 degrees. The shielding pipes can be used to further shield the beam, and the impinger can also be used to deflect a portion of the particulates, as described above.

Yet another embodiment of a method for conducting laser absorption measurements in process streams containing particulates is disclosed. As shown in FIG. 6', a launch module and a receiver module are attached to a frame continuously adjustable along vertical positions in a vertical direction and continuously adjustable along opposed, horizontal positions along a horizontal direction. As shown, the frame is selectively movable in the vertical direction so that an operating height of a sampling propagation path is selectable. The frame is further selectively movable in the horizontal direction so that an operating length of a sampling propagation path is selectable. As shown in FIG. 6', the scissors construction of the frame permits this range of motion.

The operating height of the sampling propagation path is selected, as is the operating length of the sampling propagation path. A laser beam is launched from the launch module along a laser beam propagation path extending from the launch module, along the sampling propagation path through a sampling zone containing the sample to be monitored, and to the receiver module. The beam received by the receiver module is detected and compared to the beam launched from the launch module. The method can be repeated as necessary to monitor samples across a predetermined region, thereby monitoring the process stream over multiple locations in the process.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for conducting laser absorption measurements in process streams containing particulates, the method comprising, in combination:

launching a laser beam from a launch module along a laser beam propagation path extending from the launch module, through a first shielding pipe constructed and arranged to shield the beam from the surrounding environment, along a sampling propagation path through a sampling zone containing the sample to be monitored, through a second shielding pipe constructed and arranged to shield the beam from the surrounding environment, and to a receiver module;

positioning an impinger substantially parallel to the sampling propagation path and upstream relative to the laser beam propagation path, the impinger being constructed and arranged to deflect the flow of at least a portion of the particulates in the process stream from the sampling zone;

detecting the beam received by the receiver module; and comparing the beam detected by the receiver module to the beam launched from the launch module.

2. The method as described in claim 1, wherein the impinger and the cooling pipes are in fixed relation to one another.

3. The method as described in claim 1, wherein the launch module and the receiver module are positioned in detached relation from the shielding pipes.

4. The method as described in claim 1, wherein the launch module and the receiver module are positioned in fixed relation from the shielding pipes.

5. The method as described in claim 1, wherein the first shielding pipe and the second shielding pipe have approximately equal diameters.

6. The method as described in claim 5, wherein the shielding pipes are approximately identical in shape and size.

7. The method as described in claim 1, wherein the shielding pipes are cooled.

8. The method as described in claim 1, further comprising maintaining a positive pressure flow within the shielding pipes, whereby the effective beam path length is effectively equal to the distance between the shielding pipes.

9. The method as described in claim 8, wherein the distance between the shielding pipes is selectable so as to permit selection of the effective beam path length.

10. The method as described in claim 1, further comprising interposing between the launch module and the sampling zone a first beam redirection apparatus for redirecting the beam from the launch module to the sampling zone.

11. The method as described in claim 10, further comprising interposing between the sampling zone and the receiver module a second beam redirection apparatus for redirecting the beam from the sampling zone to the receiver module.

12. The method as described in claim 11, wherein the first and second beam redirection apparatus each comprises a mirror constructed and arranged to reflect a beam of light about 90 degrees.

13. A method for conducting laser absorption measurements in process streams containing particulates, the method comprising, in combination:{PRIVATE} launching a laser beam from a launch module along a laser beam propagation path extending from the launch module, to a first beam redirection apparatus for redirecting the beam from the launch module approximately 90 degrees toward a sampling zone, through a sampling propagation path through a sampling zone containing the sample to be monitored, to a second beam redirection apparatus for redirecting the beam from the sampling zone approximately 90 degrees toward a receiver module, and to a receiver module;

detecting the beam received by the receiver module;

comparing the beam detected by the receiver module to the beam launched from the launch module;

interposing within the beam propagation path a first shielding pipe constructed and arranged to shield the beam from the surrounding environment between the launch module and the first redirection apparatus; and interposing within the beam propagation path a second shielding pipe constructed and arranged to shield the beam from the surrounding environment between the second redirection apparatus and the receiver module, wherein the first and second beam redirection apparatus each comprises a mirror constructed and arranged to reflect a beam of light about 90 degrees.

14. A method for conducting laser absorption measurements in process streams containing particulates, the method comprising, in combination:{PRIVATE} launching a laser beam from a launch module along a laser beam propagation path extending from the launch module, to a first beam redirection apparatus for redirecting the beam from the launch module approximately 90 degrees toward a sampling zone, through a sampling propagation path through a sampling zone containing the sample to be monitored, to a second beam redirection apparatus for redirecting the beam from the sampling zone approximately 90 degrees toward a receiver module, and to a receiver module;

detecting the beam received by the receiver module;

comparing the beam detected by the receiver module to the beam launched from the launch module; and interposing within the beam propagation path an impinger between the first redirection apparatus and the second redirection apparatus, the impinger extending substantially the entire length of the sampling zone, wherein the first and second beam redirection apparatus each comprises a mirror constructed and arranged to reflect a beam of light about 90 decrees.

15. A method for conducting laser absorption measurements in process streams containing particulates, the method comprising, in combination:

attaching a launch module and a receiver module to a frame continuously adjustable along vertical positions in a vertical direction and continuously adjustable along opposed, horizontal positions along a horizontal direction, the frame being selectively movable in the vertical direction so that an operating height of a sampling propagation path is selectable, the frame being selectively movable in the horizontal direction so that an operating length of a sampling propagation path is selectable;

selecting the operating height of the sampling propagation path;

selecting the operating length of the sampling propagation path;

launching a laser beam from the launch module along a laser beam propagation path extending from the launch module, along the sampling propagation path through a sampling zone containing the sample to be monitored, and to the receiver module;

detecting the beam received by the receiver module; and comparing the beam detected by the receiver module to the beam launched from the launch module.

16. The method as described in claim 15, further comprising:

repeating the steps as necessary to monitor samples across a predetermined region, thereby monitoring the process stream over multiple locations in the process.

* * * * *

UNITED STATES PATENT AND TRADEMARK OFFICE
CERTIFICATE OF CORRECTION

PATENT NO. : 6,943,886 B2
DATED : September 13, 2005
INVENTOR(S) : William A. Von Drasek, Kenneth A. Mulderink and Ovidiu Marin

It is certified that error appears in the above-identified patent and that said Letters Patent is hereby corrected as shown below:

Column 11,
Line 48, delete "{PRIVATE}".

Column 12,
Line 10, delete "{PRIVATE}".

Signed and Sealed this

Thirtieth Day of May, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,943,886 B2 | Page 1 of 1 |
| APPLICATION NO. | : 10/353786 | |
| DATED | : September 13, 2005 | |
| INVENTOR(S) | : William A. Von Drasek, Kenneth A. Mulderink and Ovidiu Marin | |

It is certified that error appears in the above-identified patent and that said Letters Patent is hereby corrected as shown below:

Col. 1, line 8,
Insert as new paragraph [0001]: --This invention was made with government support under Contract No. DE-FC36-00CH11030 awarded by the Department of Energy. The government has certain rights in this invention.--

Signed and Sealed this

First Day of August, 2006

JON W. DUDAS
*Director of the United States Patent and Trademark Office*